United States Patent
Olson et al.

(10) Patent No.: US 6,366,809 B1
(45) Date of Patent: Apr. 2, 2002

(54) DEFIBRILLATOR BATTERY WITH MEMORY AND STATUS INDICATION GUAGE

(75) Inventors: Kenneth F. Olson, Edina; William S. Parker, Maple Grove, both of MN (US)

(73) Assignee: SurVivaLink Corporation, Minnetonka, MN (US)

( * ) Notice: Subject to any disclaimer, the term of this patent is extended or adjusted under 35 U.S.C. 154(b) by 0 days.

(21) Appl. No.: 09/057,030

(22) Filed: Apr. 8, 1998

Related U.S. Application Data

(60) Provisional application No. 60/041,812, filed on Apr. 8, 1997.

(51) Int. Cl.[7] .............................. A61N 1/18; A61N 1/20; A61N 1/22; A61N 1/24; A61N 1/26
(52) U.S. Cl. ............................................ 607/5; 607/29
(58) Field of Search .............................. 607/2, 4–6, 16, 607/29, 34

(56) References Cited

U.S. PATENT DOCUMENTS

| | | | |
|---|---|---|---|
| 4,031,899 A | 6/1977 | Renirie | |
| 4,237,897 A | * 12/1980 | Beane et al. | 607/34 |
| 4,725,784 A | * 2/1988 | Peled et al. | 324/427 |
| 5,224,870 A | 7/1993 | Weaver et al. | |
| 5,342,403 A | 8/1994 | Powers et al. | |
| 5,350,317 A | 9/1994 | Weaver et al. | |
| 5,470,343 A | 11/1995 | Fincke et al. | |
| 5,483,165 A | 1/1996 | Cameron et al. | |
| 5,625,291 A | * 4/1997 | Brink et al. | 324/427 |
| 5,690,685 A | * 11/1997 | Kroll et al. | 607/5 |
| 5,721,482 A | 2/1998 | Benvegar et al. | |
| 5,741,305 A | 4/1998 | Vincent et al. | |

FOREIGN PATENT DOCUMENTS

EP  WO 97/42669  11/1997

* cited by examiner

Primary Examiner—Kennedy J. Schaetzle
(74) Attorney, Agent, or Firm—Patterson, Thuente, Skaar & Christensen, P.A.

(57) ABSTRACT

A defibrillator battery includes at least one battery cell, a housing surrounding the at least one battery cell, and a memory connected to the at least one battery cell. The memory can be positioned inside of the housing that surrounds the at least one battery cell. The defibrillator battery can be used with a defibrillator including a battery status indicator which communicates with the defibrillator battery to indicate the status of the defibrillator battery. In a method of determining defibrillator battery status using the defibrillator battery and associated battery status indicator enables an operator to always determine the remaining charge of the battery and to determine when to replace the battery. The defibrillator battery, and associated battery status indicator, insures constant readiness of an automated external defibrillator for defibrillating a patient by preventing defibrillator failure due to an unknown reduced battery charge.

8 Claims, 5 Drawing Sheets

DEFIBRILLATOR BATTERY WITH MEMORY AND STATUS INDICATION GUAGE

RELATED APPLICATION

The present invention is related to U.S. Provisional Pat. application Ser. No. 60/041,812, filed Apr. 8, 1997, the content of which is herein incorporated by reference, and priority to which is claimed according to 35 U.S.C. § 119(e).

BACKGROUND OF THE INVENTION

The present invention relates generally to defibrillators. In particular the present invention relates to a defibrillator having a battery with a memory component for use with the defibrillator to indicate the status of the battery.

Cardiac arrest, exposure to high voltage power lines and other trauma to the body can result in ventricular fibrillation which is the rapid and uncoordinated contraction of the myocardium. The use of external defibrillators to restore the heart beat to its normal pace through the application of an electrical shock is a well recognized and important tool in resuscitating patients. External defibrillation is used in emergency settings in which the patient is either unconscious or otherwise unable to communicate.

Automated external defibrillators (AEDs) are used by first responders such as police officers, paramedics and other emergency medical technicians to resuscitate cardiac arrest patients. The AEDs carried by these technicians must be quickly operational after powering up and must not provide false alarms that might delay rescue. In a high stress situation of cardiac arrest, the technician must be able to rely on the operability of the AED. Studies have shown that the chances of successfully resuscitating the patient decreases approximately ten percent per minute following cardiac arrest.

Accordingly, constant readiness of the AED is imperative. This readiness must extend to the power source of the AED, which is commonly a lithium battery. Lithium batteries are characterized by the delivery of a relatively constant voltage over a period of time which then terminates abruptly with little or no warning as the battery loses its ability to deliver energy. When using a defibrillator, an abrupt failure of the power source of a defibrillator without warning is unacceptable. Accordingly, some AEDs include the capability to perform a self test to insure that the battery has energy and that the AED can properly use that energy to deliver a shock. However, these self tests do not reveal the amount of energy left in the battery. Knowing the remaining capacity of the battery is helpful for determining how many more rescues can be performed with an AED, for determining when to replace a battery, and above all, for avoiding battery failure during use of an AED.

SUMMARY OF THE INVENTION

A defibrillator battery of the present invention includes at least one battery cell, a housing surrounding the at least one battery cell, and a memory connected to the at least one battery cell. In a preferred embodiment, the memory is positioned inside of the housing that surrounds the at least one battery cell. The defibrillator battery can be used with a defibrillator of the present invention, which includes a battery status indicator which communicates with the defibrillator battery to indicate the status of the defibrillator battery.

A method of determining the defibrillator battery status using the defibrillator battery and associated battery status indicator enables an operator to always determine the remaining charge of the battery and to determine when to replace the battery. This defibrillator battery, and associated battery status indicator, insures constant readiness of the AED for defibrillating a patient by preventing defibrillator failure due to a reduced charge battery.

DETAILED DESCRIPTION OF THE DRAWINGS

Figure 1:
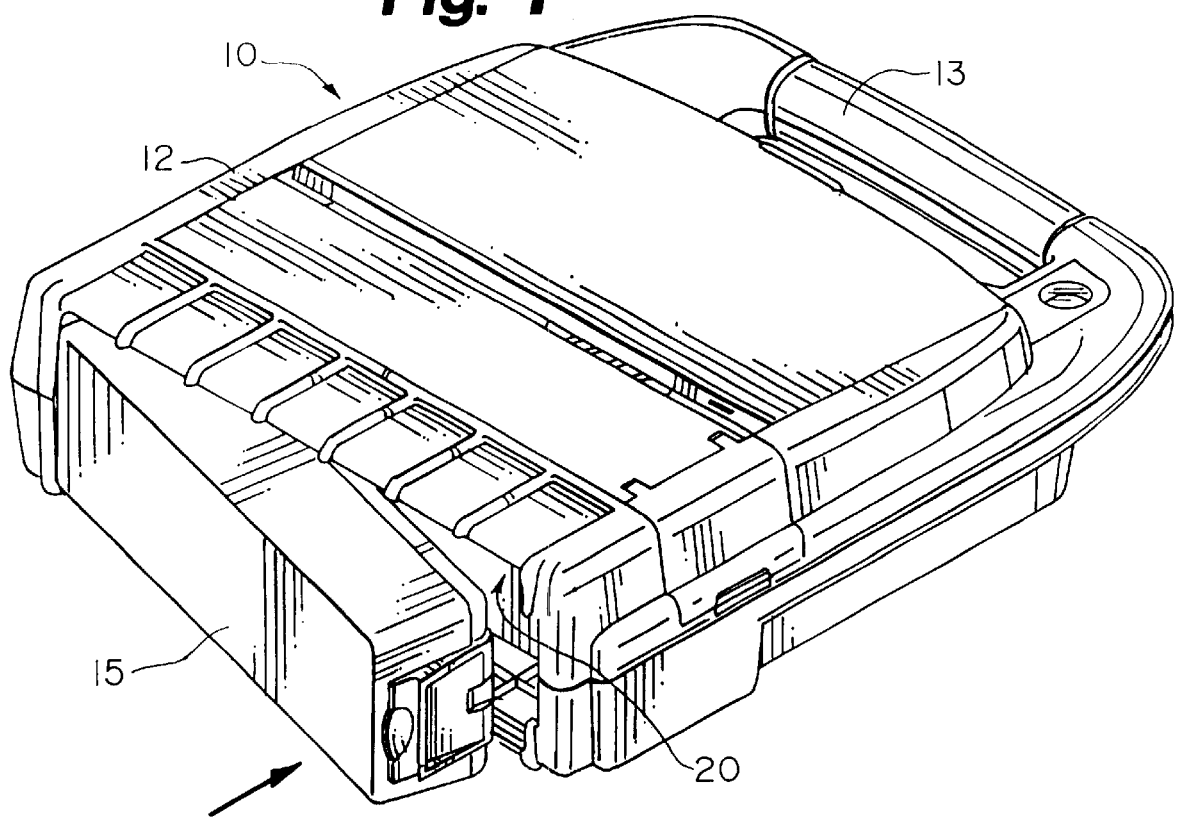
FIG. 1 is a perspective view of an automated external defibrillator having a battery pack mounted thereto.

The present invention is a defibrillator battery preferably adapted for use with automated external defibrillators (AEDs). An AED 10 in accordance with the present invention is illustrated generally in FIG. 1. As shown in FIG. 1, defibrillator 10 includes plastic case 12 with carrying handle 13. AED 10 includes a pair of electrodes (not shown) located under openable and closable lid 14 for placement on a patient for delivering a countershock with AED 10. Battery pack 15 of the present invention for powering AED 10 is removably insertable into battery receptacle 20 of AED plastic case 12.

AED 10 is used for emergency treatment of victims of cardiac arrest and is typically used by first responders. AED 10 automatically analyzes a patient's cardiac electrical signal and advises the user to shock a patient upon detection of: (1) ventricular fibrillation; (2) ventricular tachycardia; (3) or other cardiac rhythms with ventricular rates exceeding 180 beats per minute and having amplitudes of at least 0.15 millivolts. When such a condition is detected, AED 10 will build up an electrical charge for delivery to the patient to defibrillate the patient with a defibrillation shock. The operator of AED 10 is guided by voice prompts, an audible charging indicator tone, and an illuminated rescue (shock) initiation button. Olson, et al. U.S. Pat. No. 5,645,571 which is assigned to the assignee of the present application, discloses the general construction and manner of use of an AED.

Figure 2:
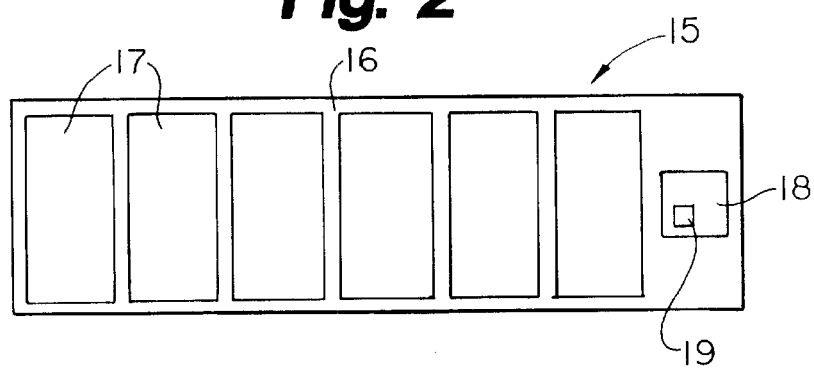
FIG. 2 is a cut away view of a battery pack illustrating individual battery cells and the memory device.

FIG. 2 schematically illustrates removably insertable battery pack 15. Battery pack 15 contains housing 16 surrounding a plurality of non-rechargeable lithium sulfur dioxide cells 17 (which may include both 12 volt and 5 volt cells). Memory component 18 is located inside housing 16 and includes a memory circuit chip 19.

Figure 3:
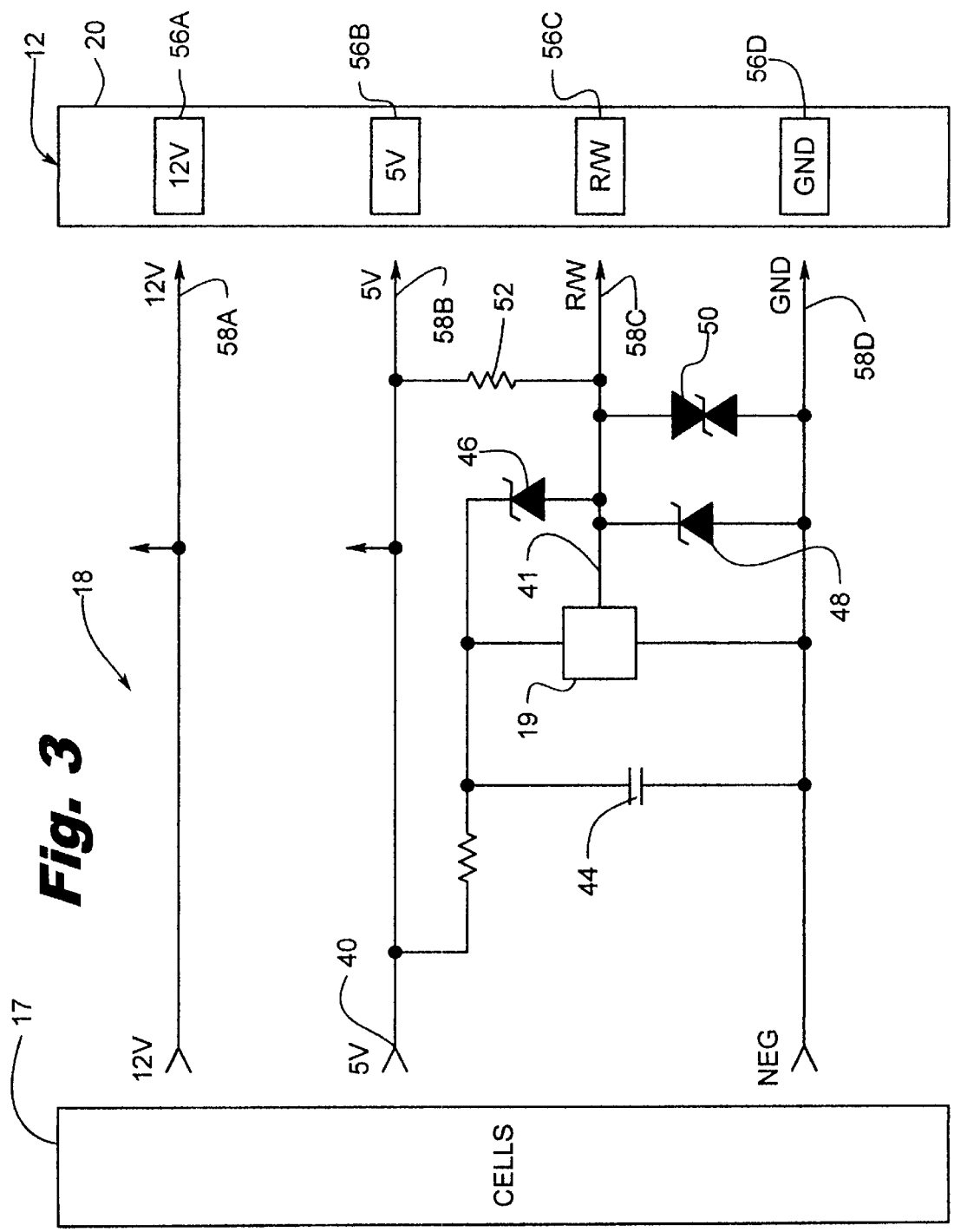
FIG. 3 is a schematic view of a circuit incorporating a memory component of the present invention.

FIG. 3 is a schematic circuit diagram illustrating the construction of memory component 18 in battery pack 15. In the preferred embodiment, circuit chip 19 is a Dallas DS2434 integrated circuit semiconductor chip, but other known memory components can also be used without departing from the spirit or scope of the present invention. Memory circuit chip 19 has three terminals including a read/write terminal 41 for accessing the memory in chip 19. Memory circuit chip 19 operates under a 5 V power supply 40 from battery cells 17 and is connected in a manner well known to those skilled in the art with resistor 42, capacitor 44, diodes 46 and 48, over voltage protection device 50, and resistor 52.

Memory component circuit 18 acts as an interface between battery cells 17 and AED 10. Accordingly, battery contact receptacle 20 of AED case 12 provides 12 V contact 56A, 5 V contact 56B, read/write contact 56C, and ground contact 56D for electrical connection to corresponding battery contacts (58A, 58B, 58C, and 58D) of memory component circuit 18 of battery pack 15. The electrical connection between read/write contact 56C of AED battery receptacle 20 and read/write contact 58C of battery pack 15 permits the read/write terminal 41 of memory chip 19 to communicate with a microprocessor of an electrical control system of AED 10. Likewise, the electrical connection of 5 V and 12 V power supply contacts 58B and 58A of battery pack 15 to 5 V and 12 V power supply contacts 56B and 56A of AED battery receptacle 20 provides power from battery cells 17 (via circuit 18) to an electrical system of AED 10.

Figure 4:
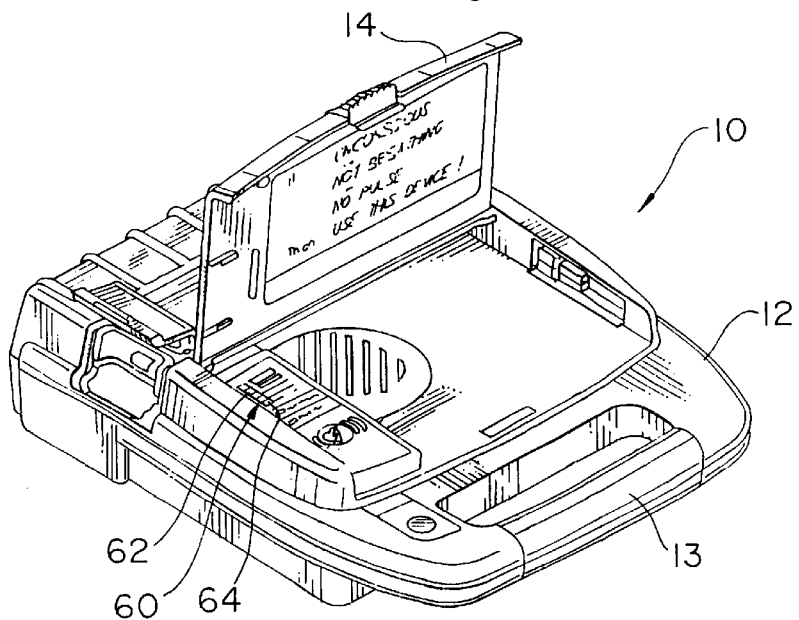
FIG. 4 is a perspective view of an AED with a battery status indicator according to the present invention.

FIG. 4 illustrates a perspective view of AED 10 with battery status indicator 60 positioned under lid 14. Status indicator 60 is electrically connectable to memory component 18 of battery pack 15 at battery contacts 56C and 58C via a microprocessor of electrical system of AED 10. As shown in greater detail in FIG. 5, status indicator 60 has a plurality of green indicator lights 62 and a red replace light 64 to indicate the relative amount of power remaining in the battery cells 17 of battery pack 15. Green indicator lights are arranged with a sufficient number of lights so that an operator can determine the proportional amount of remaining battery capacity by looking at the number of lights illuminated. For example, if indicator 62 includes four lights, illumination of all four green lights indicates full battery status while illumination of three lights indicates three-quarter battery status and illumination of two battery lights indicates one-half battery status, and so on. In this way, an operator may simply look at status indicator 60 to determine how much energy remains in battery pack 15. Moreover, when red replace indicator light 64 is illuminated, battery pack 15 must be replaced. However, memory component 18 and AED 10 can be programmed so that when the red replace light is illuminated, AED 10 can still provide enough additional shocks (e.g nine) to perform one more rescue with battery pack 15.

Figure 6:
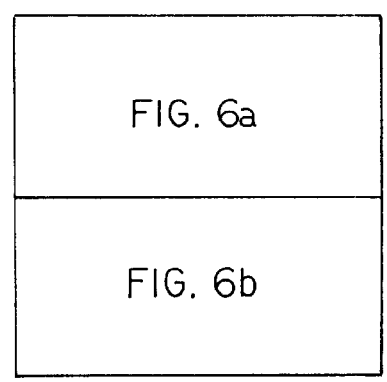
FIG. 6 is a schematic view of an electrical system of an AED incorporating a battery pack and status indicator of the present invention.
Figure 6A:
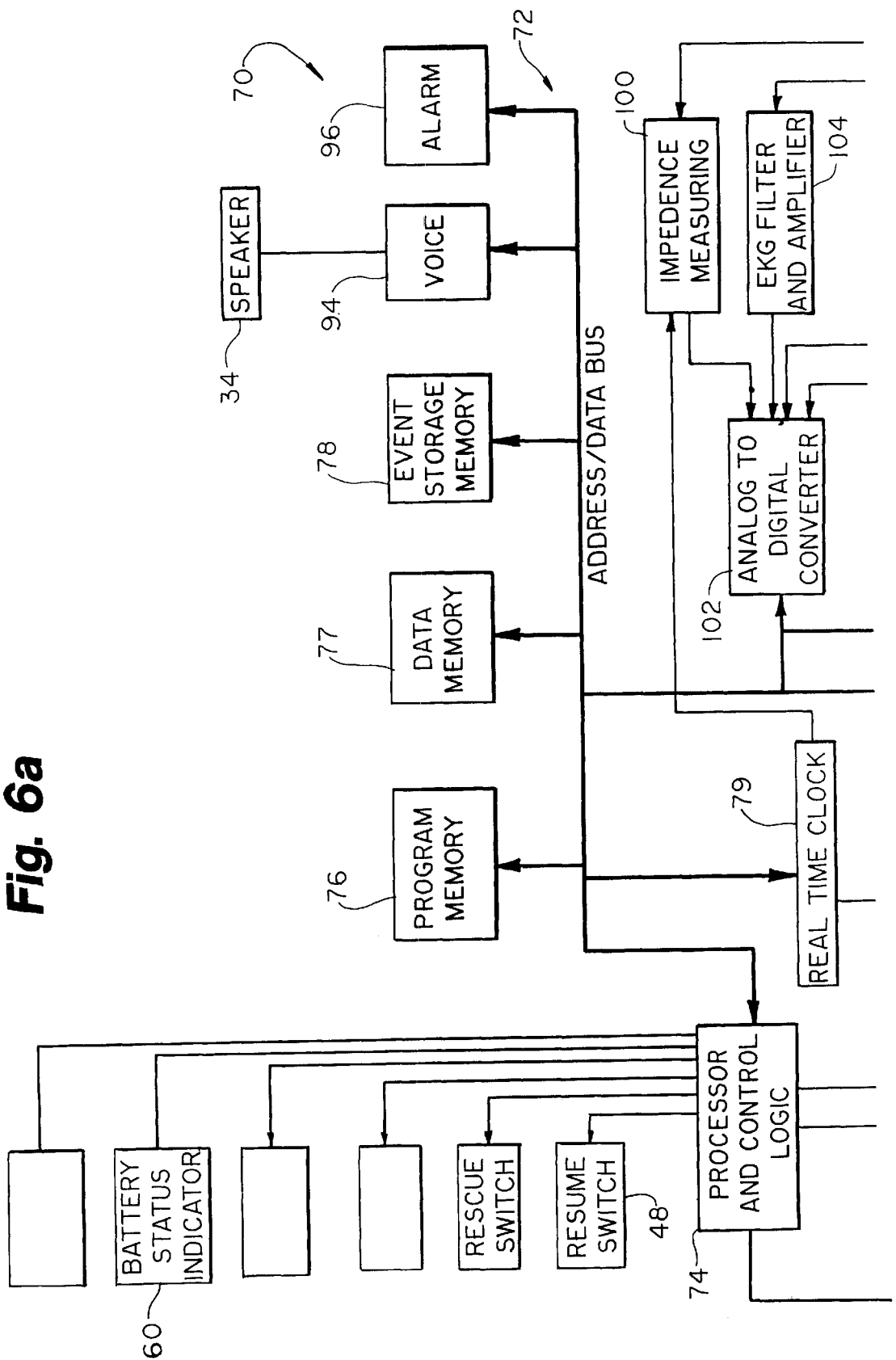
Figure 6B:
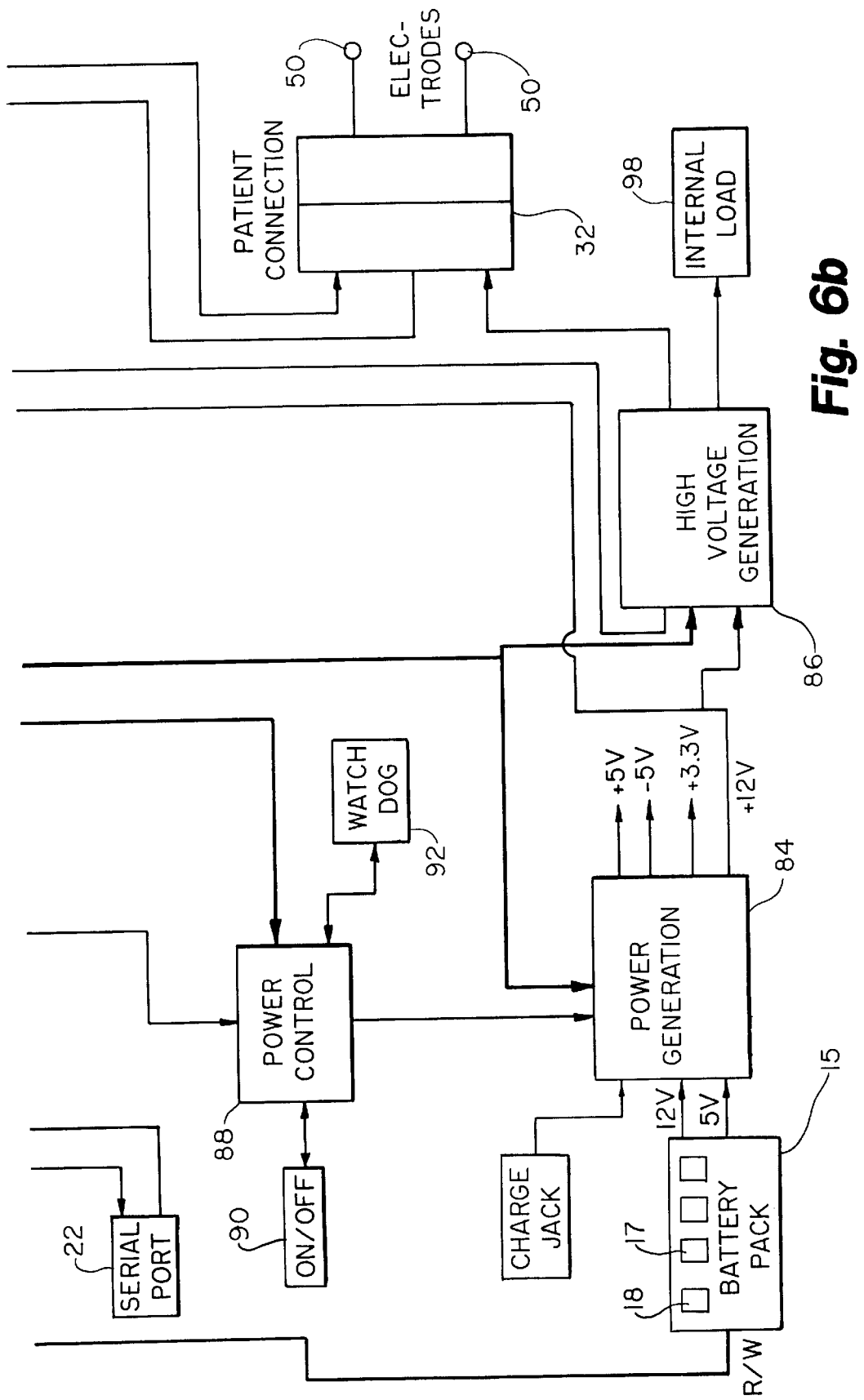

FIG. 6 is a block diagram of electrical system 70 of defibrillator 10 and further illustrates the relationship of battery pack 15 and electrical system 70 of AED 10. The general construction and operation of electrical system 70 is fully described and illustrated in U.S. Pat. No. 5, 645,571 to Olson, et al., which is hereby incorporated by reference. The overall operation of defibrillator 10 is controlled by a digital microprocessor-based control system 72 which includes a processor 74 interfaced to several components including status indicator gauge 60, program memory 76 and real time clock 79.

Battery pack 15 containing battery cells 17 is removably connectable between processor 74 and power generation circuit 84 of control system 72 and provides electrical power to control system 72. A 12 V contact 58A and 5 V contact 58B of battery pack 15 are electrically connected to power generation circuit 84 while a read/write contact 58C of memory component 18 of battery pack is electrically connected to processor 74.

Using the electrical power supplied by battery pack 15, power generation circuit 84 generates a regulated ±5 V, 3.3 V and 12 V (actually about 13.3 V) power supply for use in electrical system 70. The ±5 V supply of the power generation circuit 84 is used to power the control system 72 and most other electrical components of electrical system 70. The 3.3 V supply of the power generation circuit is coupled to nonvolatile event memory in which data representative of the patient's cardiac rhythm and the rescue mode operation of defibrillator 10 are stored. The 12 V supply is received by high voltage generation circuit 86 for charging capacitors to provide the defibrillating countershock.

The read/write connection between processor 74 and battery pack 15 enables processor 74 to read data from and write data to memory component 18 of battery pack 15. Accordingly, to determine the amount of power in remaining in battery pack 15, memory component 18 cooperates and communicates with processor 74 of the electrical control system of AED 10. Program memory 76 provides an instruction set for processor 74 to cooperate with memory chip 19 to obtain battery related data from electrical system 70 and to store and retrieve battery related information in memory chip 19 in battery pack 15.

Memory component 18 of battery pack 15 stores information regarding: (1) the initial capacity of battery cells 16; (2) a parameter of the amount of energy used per day by AED 10 in a dormant, standby mode; (3) a parameter of the amount of energy used per minute during active operation of AED 10; and (4) a parameter of the amount of energy used to charge up "shocking" capacitors of the AED 10 in preparation of delivering a shock. The memory component 18 also stores information regarding: (1) the amount of time AED 10 has been in active operation with battery pack 15; (2) the amount of time the battery pack 15 has been in service (including in standby mode and active operation); and (3) the number of charges that have been delivered by AED 10 with battery pack 15. Based on this information, the amount of energy remaining in the plurality of cells 17 is calculated.

Using the above-identified parameters and battery use information stored in memory component 18, the remaining power in battery pack 15 is calculated using memory component 18 and processor 74 by solving the following equations:

$$R12 = I12 \cdot (1 - x/A - y/2B - z/2C), \text{ and}$$

$$R5 = I5 \cdot (1 - x/A - y/B - z/C)$$

where,

I12 represents the predetermined capacity of 12 V Cells in mA hours,

I5 represents the predetermined capacity of 5 V Cells in mA hours,

A represents the predetermined energy to subtract for each high voltage charge in mA hours, B represents the predetermined energy to subtract for each minute of operation in mA hours, C represents the predetermined energy to subtract for each day in the AED in mA hours, x represents the number of high voltage charges removed from the battery 15, y represents the number of minutes the battery has been used in active operation of AED 10, z represents the number of days the battery has been in AED 10, R12 represents the number of mA hours remaining in the 12 V cells, and R5 represents the number of mA hours remaining in the 5 V cells.

Figure 5:
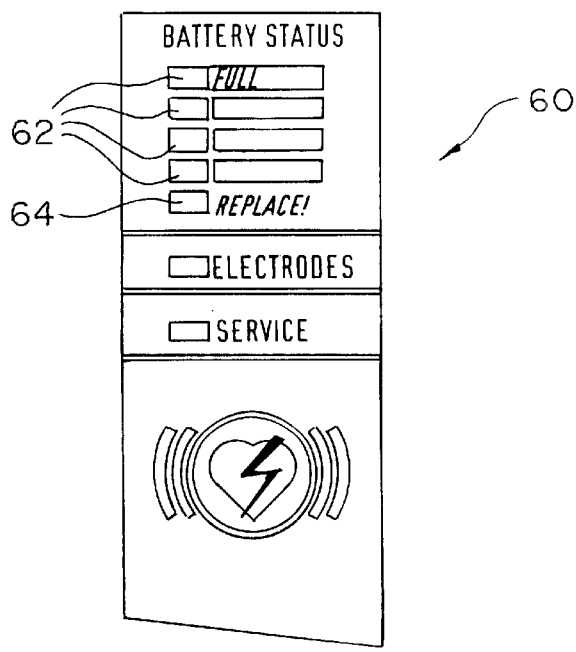
FIG. 5 is an enlarged view of the battery status indicator of FIG. 4.

Accordingly, memory component 18 stores all the information necessary to solve the equations 1 and 2 to determine the amount of power remaining in battery pack 15 in mAmp hours. This remaining amount of energy is graphically displayed on status indication gauge 60 with indicator lights 62 or light 64 (FIG. 5).

Since failure of a battery pack 15 during use of AED 10 is unacceptable, processor 74 can be instructed to write to memory component 18 that a replace battery indication is warranted when 20 percent (or other predetermined level) of remaining battery capacity is reached. In this manner, an operator is assured that battery pack 15 can be removed and replaced before capacity of battery pack 15 is drained. Using such a fail safe lower limit also requires an adjustment of calculations that determine the relative energy (full, ¾, ½, ¼) remaining in battery pack 15 so that indicator lights 62 accurately reflect the remaining capacity of battery pack 15 after accounting for the failsafe replace threshold (e.g. 20% capacity).

Since battery pack 15 includes memory component 18 built into housing 15, memory component 18 always stays with battery cells 17. Accordingly, if battery pack 15 is removed from an AED 10 after partial use, the history of use of the battery pack 15 is carried with battery pack 15. Accordingly, if partially used battery pack 15 is placed in an AED 10, processor 74 of AED 10 can read memory component 18 to determine when the battery was first previously used and the remaining energy capacity of partially used battery pack 15 as well as display the remaining energy capacity on multi-level status indicator gauge 60.

A combination of memory component 18 in battery pack 15 and processor 74 provides ongoing indication of remaining battery energy as displayed on indicator gauge 60. However, periodic direct tests of the voltage of battery cells 17 is also desirable to insure proper functioning of battery pack 15 and AED 10.

Accordingly, battery voltage level sensing circuits are incorporated into power generation circuit 84 (and coupled to processor 74) and operate independently of battery status indicator gauge 60. The voltage level sensing circuits operate as a failsafe mechanism to provide low battery level signals to processor 74 whenever the voltage levels of battery cells 17 are less than a predetermined value. If a low voltage level signal is sent to processor 74, processor 74 then updates memory component 18 of battery pack 15 to reflect a battery failure. This battery failure is displayed on status indicator gauge 60 by illuminating the replace battery indicator light 64. Accordingly, the battery voltage level sensing circuits can override a calculated value of the remaining energy in battery cells 17 obtained using the above equations.

Moreover, if memory component 18 of battery pack 15 fails or processor 74 otherwise cannot read or write to memory component 18 of battery pack 15 (e.g. due to poor electrical contact), then processor 74 is programmed (via program memory 79) to assume that battery pack 15 is nonfunctional. In response, processor 74 illuminates replace light indicator 64 to indicate on status indicator gauge 60 that battery pack 15 must be replaced. Accordingly, in cooperation with memory component 18 of battery pack 15, processor 74 and status indicator gauge 60 insures that an operator will receive information to replace a battery regardless of the source of failure (e.g. battery cell 17, memory component 18, or other component of battery pack 15).

The battery voltage level test is performed at or during several events. First, the battery voltage test is performed just before use of AED 10 and just after use of AED 10, as well as during a daily and weekly self test of AED 10 as described below.

The first event of directly testing battery voltage levels occurs during a rescue mode operation of defibrillator 10 when an operator opens lid 14 to begin a rescue and access the electrodes of AED 10. The opening of the lid 14 is detected by lid switch 90, which effectively functions as an on/off switch. Processor 74 then begins its rescue mode operation which includes performing a lid opened self-test.

During the lid opened self-test, processor 74 checks the charge state of battery pack 15 as well as other components such as the interconnection and operability of electrodes 50. As described above, the charge state of battery pack 15 is checked by monitoring the voltage level signals provided by power generation circuit 84. If battery pack 15 is determined to have a low charge, lights 64 on status indicator gauge 60 is illuminated by processor 74 and battery memory 18 is updated by processor to store a "replace battery" status.

If the lid opened self-test is successfully completed, processor 74 permits continued operation of AED 10 in a rescue mode of operation. After detecting an impedance indicating the proper placement of electrodes 50, an automatic sequence of analyzing heart rhythm of the patient for a shockable rhythm and prompting use of CPR as appropriate when a nonshockable rhythm is present. When a shockable cardiac rhythm is detected, processor 74 begins a first charge sequence of charging high voltage generation circuit 86 and initiating a first shock sequence to the patient with cautioning voice prompts to press a rescue/shock button and stand clear. Operator actuation of rescue switch 18 results in the application of a defibrillation pulse of preferably about 200 joules to the patient to complete the first series of analyze/charge/shock sequences. Following the first series of analyze/charge/shock sequences, processor 74 ends rescue mode operation of defibrillator 10 after a subsequent series of analyze/charge/shock sequences have been performed, or lid 14 is closed.

A lid closed self-test is also initiated and performed by processor 74 when lid 14 is closed following rescue mode operation of the defibrillator 10. During the lid closed self-test processor 74 performs a comprehensive check of the status and functionality of defibrillator 10, including the charge state of battery pack 15. The state of battery pack 15 is checked in a manner like that described for the lid opened self-test.

Of course, both the lid open and lid closed test consume energy from battery pack 15. Processor 74 tracks this use of battery energy using the parameters identified above and updates memory component 18 of battery pack 15 so that status indicator gauge 60 accurately reflects the ongoing battery usage of AED 10.

In addition, a daily self test and a weekly self test of AED 10 is performed during which the voltage level of battery cells 17 of battery pack 15 is checked. The daily self-test is initiated and performed by processor 74 at a predetermined time each day (i.e., every twenty-four hours) while the weekly self test occurs at a predetermined time one day each week. Processor 74 illuminates replace battery indicator 64 of status gauge indicator 60 and activates alarm 96 if faults are identified during the daily self-test or weekly self test. The weekly self test also includes a test of the ability of high voltage generation circuit 86 to sequentially operate in its charge and discharge modes, with the charge being dumped to internal load 98. Processor 74 updates memory component 18 of battery pack 15 with the number of charges (parameter x in equations) so that memory component 18 and status indicator gauge 60 reflect the energy capacity used during the weekly self test.

Other parameters can also be stored in memory component 18 in battery pack 15. These parameters include the time and date the battery pack 15 was installed in the AED 10 as well as a serial number of the battery for tracking the origin of the battery. Real time clock 79 (with its own long term internal battery) provides processor 74 with the time/date data for writing and storage in memory component 18. Moreover, the serial number of AED 10 can be written and stored in battery pack 15 to identify the AED 10 in which battery pack 15 was installed.

In alternative embodiment, memory component 18A can be located outside of battery pack 15A. For example, memory component 18A is preferably located in AED case 12 as part of electrical system 70 and is electrically connected to processor 74 and battery cells 17 in a manner similar to that shown in FIG. 3. Upon placement of battery pack 15A in AED 10, processor 74 writes to memory component 18A to store a full battery status and begins tracking usage of battery pack 15A in a manner similar to that described above for memory component 18 and displays the remaining battery capacity on status indicator gauge 60. In combination with battery pack 15A and memory component 18A, processor 74 uses equations 1 and 2 as described above to determine the remaining battery capacity and stores that information to memory component 18A. However, since memory component 18A does not travel with battery pack 15A as in the first embodiment, the battery energy calculation is effective only for a new battery pack 15A (with full initial capacity) installed in AED 10. Nevertheless, although memory component 18A does not travel with the battery pack 15A, the memory component 18A and status indicator gauge 60 permit ongoing visual indication of the remaining battery capacity of battery pack 15A.

Finally, regardless of how a memory component (like memory component 18) is implemented for use with a microprocessor of an AED to track and store battery usage (e.g in the battery pack 15, in the AED case 12, or other location) the present invention includes a defibrillator case having a multi-level fuel indicator gauge for use with a lithium battery cell. The defibrillator graphically displays the relative amount of energy remaining in a lithium battery being used in the defibrillator. A multi-level battery status indicator is significant in an AED since lithium battery cells are characterized by providing a constant voltage until abrupt failure.

A defibrillator with a battery pack and status indicator gauge of the present invention offers considerable advantages. First, a memory component of the present invention, when used with a lithium battery, enables an operator to determine the remaining energy capacity (in mAmp hours) in the lithium battery rather than merely apply a periodic voltage test to determine battery readiness. Second, a multi-level battery gauge of the present invention permits a defibrillator to continuously display the relative remaining battery capacity of a lithium battery used with defibrillator. Third, when a memory component is incorporated into a battery housing with a lithium battery, the memory component always travels with lithium battery so that the battery carries with it a history of its use including its remaining capacity. This permits a battery to be removed from one defibrillator and used in another defibrillator while still maintaining knowledge of the remaining capacity of the battery. Fourth, the memory component is implemented without displacing the conventional voltage battery test for determining lithium battery readiness in the defibrillator.

Although the present invention has been described with reference to preferred embodiments, those skilled in the art will recognized that changes can be made in form and detail without departing from the spirit and scope of the invention.

What is claimed is:

1. A defibrillator battery comprising:
   at least one battery cell;
   a housing surrounding the at least one battery cell; and
   a memory connected to the at least one battery cell, the memory storing a first parameter of how much energy is used by a defibrillator in a standby mode on a daily basis, a second parameter of how much energy is used by the defibrillator during active operation per minute, and a third parameter of how much energy is used by the defibrillator charging up a capacitor bank.

2. The battery as in claim 1 wherein the memory is mounted in the housing.

3. The battery of clam 1 wherein the memory is capable of storing an initial energy capacity of the battery.

4. The battery of claim 1 wherein the memory is capable of storing a serial number of the battery, an initial use date the battery was placed in service, and a voltage that indicates the battery is dead under high current.

5. A defibrillator battery comprising:
   at least one battery cell;
   a housing surrounding the at least one battery cell; and
   a memory connected to the at least one battery cell wherein the memory stores how many minutes a defibrillator has been in operation, how many days a defibrillator has been in standby mode, and how many charges have been delivered by a defibrillator.

6. A defibrillator battery comprising:
   at least one battery cell;
   a housing surrounding the at least one battery cell; and
   a memory connected to the at least one battery cell wherein the amount of energy remaining in the battery is determined by solution of the equations, $$R12 = I12 \cdot (1-[x/A]-[y/2B]-[z/2C]), \text{ and}$$

$$R5 = I5 \cdot (1-[x/A]-[y/B]-[z/C])$$

where I12 represents the capacity of 12 V Cells in mA hours,
   I5 represents the capacity of 5 V Cells in mA hours,
   A represents the energy for each high voltage charge of a defibrillator in mA hours,
   B represents the energy for each minute of active operation of a defibrillator in mA hours,
   C represents the energy for each day the battery is in a defibrillator in a standby mode in mA hours,
   x represents the number of high voltage charges removed from the battery,
   y represents the number of minutes the battery has been used for active operation,
   z represents the number of days the battery has been in a defibrillator,
   R12 represents the number of mA hours remaining in the 12 V battery cells, and
   R5 represents the number of mA hours remaining in the 5 V battery cells.

7. A method of monitoring status of a lithium battery in an automated external defibrillator comprising:
   providing an automated external defibrillator having a battery status indication gauge and a lithium battery;
   tracking an amount of use of the battery in the defibrillator and determining the remaining energy capacity of the battery by comparing the amount of use against predetermined energy use parameters of the battery and the defibrillator;
   displaying the remaining energy capacity of the battery by illumination of the battery status indication gauge.

8. The method of claim 7 wherein the step of tracking and determining further comprises storing the amount of use and the predetermiend energy use parameters in memory associated with the battery.

* * * * *